(12) United States Patent
Shanks et al.

(10) Patent No.: US 6,670,510 B2
(45) Date of Patent: Dec. 30, 2003

(54) PROCESS FOR PREPARING 2,5-DIMETHOXY BENZALDEHYDE

(75) Inventors: Thomas Elbert Shanks, Piney Flats, TN (US); Robert Joseph Maleski, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/124,856

(22) Filed: Apr. 18, 2002

(65) Prior Publication Data

US 2003/0199714 A1 Oct. 23, 2003

(51) Int. Cl.[7] ............................................. C07C 45/64
(52) U.S. Cl. ........................ 568/433; 568/438; 568/426
(58) Field of Search ................................ 568/433, 438, 568/426

(56) References Cited

U.S. PATENT DOCUMENTS

| | | | |
|---|---|---|---|
| 3,652,675 A | * | 3/1972 | Rao et al. .................... 568/442 |
| 3,691,210 A | | 9/1972 | Solodar |
| 3,867,458 A | | 2/1975 | Imai et al. |
| 4,662,999 A | | 5/1987 | Opaskar et al. |

FOREIGN PATENT DOCUMENTS

| | | |
|---|---|---|
| EP | 529870 | 3/1993 |
| GB | 853482 | 11/1960 |
| GB | 1069409 | 5/1967 |

OTHER PUBLICATIONS

Acta Chemica Scandinavica, No Month Provided 1999, vol. 53, pp. 258–262.
Miller et al. J. Org. Chem., No Month Provided 1981, vol. 46, pp. 4751–4753.
Miller et al., Synthesis, Nov. 1981, pp. 894–895.
Elwahy, Tetrahedron, No Month Provided 2000, vol. 56, pp. 897–907.

* cited by examiner

*Primary Examiner*—Rosalynd Keys
(74) *Attorney, Agent, or Firm*—Michael J. Blake; Bernard J. Graves, Jr.

(57) ABSTRACT

The present invention recites a process for the of 2,5-dimethoxy-benzaldehyde by reacting a 2-hydroxy-5 methoxy-benzaldehyde with a suitable metal hydroxide in the presence of a suitable solvent to make a metal salt of 2-hydroxy-5-methoxy benzaldehyde comprising. The invention further provides a method for alkylating said metal salts with dimethylsulfate in the presence of a suitable solvent so as to provide a 2,5-dimethoxy benzaldehyde.

19 Claims, No Drawings

PROCESS FOR PREPARING 2,5-DIMETHOXY BENZALDEHYDE

FIELD OF THE INVENTION

This invention relates generally to a process for preparing and isolating metal salts of 2-hydroxy-5-methoxy benzaldehyde from crude, or impure, 2-hydroxy-5-methoxy benzaldehyde and for preparing 2,5-dimethoxy benzaldehyde from those salts.

BACKGROUND OF THE INVENTION 2,5-dimethoxybenzaldehyde finds use as an intermediate for the preparation of developing agents for black-and-white and color photography (UK 853,482); as an intermediate for textile dyes (U.S. Pat. No. 3,691,210); and as an additive that can improve the performance of electroplating baths (U.S. Pat. No. 4,662,999). Numerous methods for its preparation have been reported, the two most common being direct formylation of 1,4-dimethoxybenzene (UK 1,069,409; Reaction 1, below), and alkylation of 2-hydroxy-5-methoxy benzaldehyde with dimethyl sulfate (U.S. Pat. No. 3,867,458; Reaction 2, below).

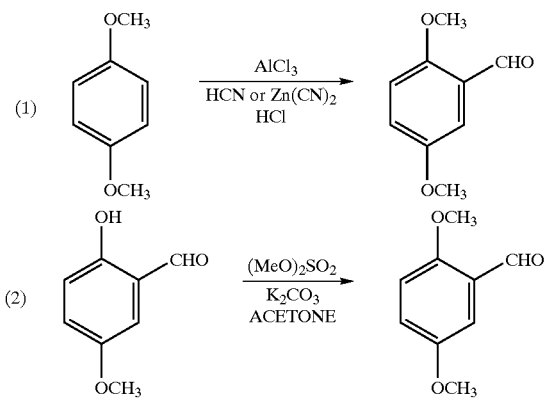

The first of these methods suffers from the need to use highly toxic hydrogen cyanide or zinc cyanide under acidic conditions, thus necessitating the use of expensive equipment to first contain and then destroy the toxic gases. The second of these methods overcomes the need to handle toxic gases, but the 2-hydroxy-5-methoxy benzaldehyde starting material must be purified before conversion to the title product. As such, an expensive and time consuming distillation step is necessary to achieve the appropriate purity (see, Comparative Examples 1(a) and 1(b)). Therefore, the need still exists for a process for preparing 2,5-dimethoxy benzaldehyde that avoids the use of highly toxic hydrogen cyanide or zinc cyanide while simultaneously eliminating the need for an expensive and time-consuming distillation step.

SUMMARY OF THE INVENTION

Among other aspects, the present invention is based on the discovery of a novel method for preparing and isolating a pure, or at least substantially pure, reactive sodium or potassium salt of 2-hydroxy-5-methoxy benzaldehyde. The ability to alkylate these sodium or potassium salts in turn provides an economically favorable method to obtain equally high or higher yields of 2,5-dimethoxy benzaldehyde by avoiding the need for costly distillation of the 2-hydroxy-5-methoxy benzaldehyde prior to a subsequent alkylation. Additionally, alkylating the potassium or sodium salt of 2-hydroxy-5-methoxy benzaldehyde proceeds at a lower temperature than the alkylation reaction of the pure aldehyde counterpart, which similarly results in a reduced overall cost for the alkylation step.

Accordingly, the present invention provides a process for preparing 2,5-dimethoxy benzaldehyde comprising the steps of: (a) reacting a crude 2-hydroxy-5-methoxy benzaldehyde with a metal hydroxide to produce a reaction mixture comprising a metal salt of 2-hydroxy-5-methoxy benzaldehyde; (b) separating the metal salt of 2-hydroxy-5-methoxy benzaldehyde from the reaction mixture of step (a) to obtain an at least substantially pure metal salt of 2-hydroxy-5-methoxy benzaldehyde; and (c) alkylating the metal salt of 2-hydroxy-5-methoxy benzaldehyde of step (b) with dimethylsulfate to produce 2,5-dimethoxy benzaldehyde.

Additional advantages and embodiments of the invention will be obvious from the description, or may be learned by practice of the invention. Further advantages of the invention will also be realized and attained by means of the elements and combinations particularly pointed out in the appended claims. Thus, it is to be understood that both the foregoing general description and the following detailed description are exemplary and explanatory of certain embodiments of the invention and are not restrictive of the invention as claimed.

DETAILED DESCRIPTION OF THE INVENTION

The present invention may be understood more readily by reference to the following detailed description and the examples provided herein. It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a", "an", and "the" comprise plural referents unless the context clearly indicates otherwise. For example, reference to a component in the singular is intended to comprise a plurality of components.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about" or "approximately", it will be understood that the particular value forms another embodiment.

The phrase "substantially pure" as applied to the metal salt of 2-hydroxy-5-methoxy benzaldehyde means a purity of at least about 70% on a weight % assay basis or, alternatively, at least about 95% based on HPLC area %. In more preferred embodiments, the purity is at least 80% or greater or, still more preferably, at least 90% on a weight % assay basis; when measured by HPLC area %, the purity is more preferably at least 98% or, still more preferably, at least 99%.

Throughout this application, where publications are referenced, the disclosures of these publications in their entireties are hereby incorporated by reference into this application in their entirety to more fully describe the state of the art to which this invention pertains.

As discussed above, the present invention provides a process for preparing 2,5-dimethoxy benzaldehyde comprising the steps of: (a) reacting a 2-hydroxy-5-methoxy benzaldehyde with a metal hydroxide to produce a reaction mixture comprising a metal salt of 2-hydroxy-5-methoxy benzaldehyde; (b) separating the metal salt of 2-hydroxy-5-methoxy benzaldehyde from the reaction mixture of step (a) to obtain an at least substantially pure metal salt of 2-hydroxy-5-methoxy benzaldehyde; and (c) alkylating the metal salt of 2-hydroxy-5-methoxy benzaldehyde of step (b) with dimethylsulfate to produce 2,5-dimethoxy benzaldehyde.

A common method for preparing the 2-hydroxy-5-methoxy benzaldehyde comprises reacting a magnesium salt of 4-methoxy phenol with formaldehyde or paraformaldehyde, which generates formaldehyde under the conditions of the reaction, followed by acidic quench and distillation or chromatography as disclosed in European Patent Application 92307354.8, and also disclosed in Acta Chemica Scandinavia, 53, 258, 1999, which references are hereby incorporated by reference in their entireties for all purposes. (See, Reaction (I) set forth below.) In the EP application referenced above, the source of Mg is magnesium methoxide; and in the Acta Chemica Scandinavia article, it is magnesium chloride.

Reaction (I)

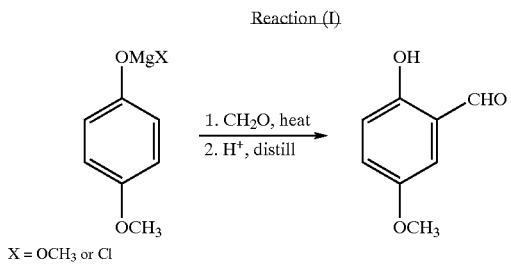

X = OCH₃ or Cl

Any inorganic acid strong enough to protonate the product phenoxide salt is suitable. Typically, a distillation or chromatography of the 2-hydroxy-5-methoxy benzaldehyde product has been necessary in order to achieve the desired level of purity prior to further processing to the title product. The Acta Chemica Scandinavia article professes a yield of 97% for the subject compound, which indicates few by-products. However, repetition of that disclosure (Example 1) indicates the presence of several impurities that lower the assay and the yield, which, when using the prior art process, necessitates a purification step prior to use in an alkylation reaction, (See, Comparative Examples 1a and 1b).

In accordance with the invention, Applicants have discovered that unpurified, or crude, reaction product obtained from the formation of the 2-hydroxy-5-methoxy benzaldehyde, for example, as set forth above can be treated in situ with a suitable metal hydroxide to generate pure, or at least substantially pure, metal salts of 2-hydroxy-5-methoxy benzaldehyde. (See Reaction (II), set forth below.) The resulting metal salts of 2-hydroxy-5-methoxy benzaldehyde can then be separated by any known means for separating a salt from a reaction mixture, such as by filtration, and are suitable for use in the above-mentioned alkylation with dimethylsulfate to thereby produce the 2,5-dimethoxy benzaldehyde.

Reaction (II)

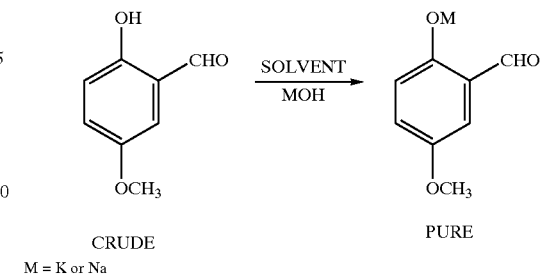

M = K or Na

Our discovery eliminates the need for a costly and time consuming distillation or chromatography step that was previously required in order to obtain pure 2-hydroxy-5-methoxy benzaldehyde suitable for use in an alkylation reaction.

The preferred metal hydroxides suitable for use in the present invention include, without limitation, sodium hydroxide and potassium hydroxide. The amount of metal hydroxide base to be employed in the reaction should be adjusted so as to be close to approximately one molar equivalent relative to the amount of 2-hydroxy-5-methoxy benzaldehyde in the solution. Too small an amount could potentially lead to lower than desired product yields. Likewise, too high a concentration of metal hydroxide could potentially lead to increased product instability or to decreased product purity.

More specifically, the amount of metal hydroxide employed should be from approximately 0.90 to approximately 1.10 equivalents relative to the amount of 2-hydroxy-5-methoxy benzaldehyde employed. However, in a preferred embodiment, the amount of metal hydroxide used is approximately from about 0.92 to about 1.07 equivalents, or more preferably, from about 0.95 to about 1.05 equivalents. In still a more preferred embodiment, the amount of metal hydroxide employed is from about 0.98 to about 1.02 equivalents relative to the amount of 2-hydroxy-5-methoxy benzaldehyde employed. It should also be understood that it is within the scope of the present invention for any one of the lower end ranges listed above to be paired with any one of the upper end ranges listed above.

It should also be noted that the metal hydroxide component can be introduced into the reaction as either a concentrated solution in water, a concentrated solution in methanol, or even as a dry, or at least substantially dry, solid. However, if a solid form of the metal hydroxide is used, it is advantageous, although optional, to reduce the particle size and/or increase the surface area of the solid prior to use in the reaction mixture. To this end, any means for reducing the particle size of the solid known to one of ordinary skill in the art can be used, such as grinding or pulverizing the solid in a mortar.

In a preferred embodiment, a suitable solvent is employed in forming the metal salts of 2-hydroxy-5-methoxy benzaldehyde. Such suitable solvents generally are any polar organic solvents capable of dissolving crude 2-hydroxy-5-methoxy benzaldehyde. Such solvents can include any solvent in which the product metal salt has a limited solubility and in which both the metal hydroxide and the starting 2-hydroxy-5-methoxy benzaldehyde have good solubility. Examples of suitable solvents include, without limitation, lower molecular weight alcohols such as isopropyl alcohol or n-butanol, ketones such as acetone or methyl ethyl ketone, esters of acetic acid such as ethyl acetate or n-propyl acetate, glycols such as ethylene glycol or propylene glycol, or ethers such as dimethoxy ethane, dimethoxy methane, 2-methoxy ethanol, and 2-hydroxy-1-methoxypropane. In a preferred embodiment, the at least one suitable solvent is acetone and/or ethyl acetate.

The concentration of the 2-hydroxy-5-methoxy benzaldehyde in the at least one suitable solvent should be adjusted to provide an easily stirred slurry of the resulting metal salt. Typically, initial concentrations of the 2-hydroxy-5-methoxy benzaldehyde can be from about 5% to about 35%, or in other embodiments from approximately 10% or 15% to approximately 20%, 25% or 30%. Again, it should be understood that it is within the scope of the present invention for any one of the lower end concentration percentages to be paired with any one of the upper end concentrations. However, in a preferred embodiment, the concentration of the 2-hydroxy-5-methoxy benzaldehyde is approximately from 10 to approximately 30%. In still a more preferred embodiment, the concentration of 2-hydroxy-5-methoxy benzaldehyde is from about 15 to about 25%.

It should also be understood that the preparation of the metal salts of 2-hydroxy-5-methoxybenzaldehyde can be accomplished by introducing the aldehyde, metal hydroxide and solvent into a reaction environment in any desired order. For example, in one embodiment, the aldehdye can be diluted with a suitable solvent followed by subsequent addition of the metal hydroxide. In an alternate embodiment, the metal hydroxide is introduced into a suitable solvent followed by the subsequent addition of 2-hydroxy-5-methoxy benzaldehyde. In still another embodiment, the metal hydroxide and diluted 2-hydroxy-5-methoxy benzaldehyde can be premixed followed by the subsequent addition of the suitable solvent.

In accordance with these embodiments, it is preferred that the temperature at which the hydroxide is introduced into the suitable solvent and/or 2-hydroxy-5-methoxy benzaldehyde should be relatively moderate in order to reduce the probability of undesired product decomposition. For example, suitable metal hydroxide addition temperatures include any temperature from approximately −10° C. to approximately 45° C. In those embodiments employing solid metal hydroxide, the preferred addition temperature is from approximately 15° C. to approximately 35° C., and more preferably from about 20° C. to approximately 30° C. In those embodiments employing metal hydroxide solutions, the preferred addition temperature is from about −5° C. to about 20° C., and more preferably approximately 0° C. to approximately 15° C. It should also be understood that it is within the scope of the present invention for any one of the lower end ranges listed above to be paired with any one of the upper end ranges listed above.

In accordance with the present invention, it has been discovered that in certain instances the formation of the desired salt may occur relatively quickly and, as such, the required reaction time can be relatively short. For example, the reaction time required for the salt formation can be from as little as approximately 0.25 hours to as long as approximately 3.0 hours. In one embodiment, the reaction time required for salt formation is from approximately 0.5 to approximately 1 hour.

The filtration of the product metal salt of 2-hydroxy-5-methoxy benzaldehyde from the reaction mixture should be performed at a temperature that will minimize the loss of the metal salt product due to partial solubility in the filtrate. As such, suitable filtration temperatures according to the invention can be from approximately −20° C. to approximately 20° C., including such temperatures as about −15 or −10 to about 10 or 15° C. In a preferred embodiment, the filtration temperature should be approximately 0° C. to approximately 10° C.

The alkylation of the metal salt of 2-hydroxy-5-methoxy benzaldehyde with dimethylsulfate can be performed in any solvent or combination of solvents in which the metal salt has sufficient solubility and the dimethylsulfate has good stability. For example, suitable solvents include lower molecular weight alcohols such as methanol, isopropanol or n-butanol; ketones such as acetone or methyl ethyl ketone; esters of acetic acid such as ethyl acetate or n-propyl acetate; glycols such as ethylene glycol or propylene glycol; and/or ethers such as dimethoxy ethane, dimethoxy methane, 2-methoxy ethanol, and 2-hydroxy-1-methoxypropane. Additional suitable solvents also include solvent mixtures comprising: (1) toluene and dimethylformamide; or (2) heptane and dimethylformamide. In a preferred embodiment, the solvent(s) used for the alkylation step include(s) acetone and/or isopropanol.

The amount of dimethyl sulfate used in the alkylation reaction should be at least approximately 1 equivalent relative to the amount of salt of the 2-hydroxy-5-methoxybenzaldehyde employed. If the solvent chosen is one that can potentially react competitively with the dimethyl sulfate, an excess of the dimethylsulfate should be used. Accordingly, a suitable amount of dimethylsulfate includes approximately 1 to 2 equivalents relative to the amount of metal salt employed. In a preferred embodiment, the amount of dimethyl sulfate is approximately 1.1 to approximately 1.5 equivalents relative to the amount of metal salt employed.

The temperature of the reaction mixture during the alkylation step should also be adjusted according to the chemical and physical properties of the solvent(s) and/or solvent mixture used. To this end, the optimum reaction conditions will be known or readily obtained by one of ordinary skill in the art without requiring any undue experimentation. However, in general, suitable reaction mixture temperatures can be from approximately 10° C. to approximately 80° C. In a preferred embodiment, the temperature of the reaction mixture during the alkylation reaction is from approximately 30° C. to approximately 50° C. It should also be understood that it is within the scope of the present invention for any one of the lower end ranges listed above to be paired with any one of the upper end ranges listed above.

The required reaction time for the alkylation step is predominantly influenced by the chemical and physical properties of the solvent(s) and/or solvent mixture used. Therefore, it should again be understood that required reaction times will be known or readily obtained by one of ordinary skill in the art without requiring any undue experimentation. However, in general, it is desired that the reaction conditions should be chosen such that the alkylation reaction is at least substantially complete within approximately 1 to approximately 6 hours. In a preferred embodiment, the reaction time required for the alkylation step is approximately 1 to approximately 2 hours.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.); however, some errors and deviations may have occurred. Unless indicated otherwise, parts are parts by weight, temperature is degrees C or is at ambient temperature, and pressure is at or near atmospheric.

The amount of a compound or property as provided herein means that such amount is capable of performing the function of the compound or property for which an amount is expressed. As will be pointed out below, the exact amount required will vary from process to process, depending on recognized variables such as the compounds employed and the processing conditions observed. However, an appropriate amount may be determined by one of ordinary skill in the art using routine experimentation.

Example 1

Preparation of Crude 2-Hydroxy-5-Methoxybenzaldehyde

A mixture of 600 g of acetonitrile, 186.2 g of 4-methoxyphenol (1.5 moles) and 214 g (2.25 moles) of anhydrous magnesium chloride was warmed to 45° C. and 227.4 g (2.25 moles) of triethylamine was added dropwise at that temperature. Paraformaldehyde (150 g, 4.75 moles) was then added and the reaction was heated to reflux. Methanol was removed over 3 hours by distillation, using a 10-inch column packed with Penn-State packing. The weight of the methanol removed (vapor temperature 60–65° C.) was 130 g. The solution was cooled to 60° C. and added to 900 mL of water. The solution was acidified with 240 mL of conc. HCl and extracted with 150 g of ethyl acetate. The ethyl acetate solution was washed once with 300 mL of tap water, clarified through diatomaceous earth, and stripped on a rotary evaporator at 10 mm pressure and 85° C. bath temperature. The weight of the product was 206.5 g, the liquid chromatograph area percent was 86%, and liquid chromatograph weight percent was 82%. The overall assay yield was 74%.

Comparative Example 1(a)

Use of Crude 2-Hydroxy-5-Methoxybenzaldehyde

The above crude oil (6.1 g, 81% assay, 0.33 moles), 25 mL of acetone, 6.8 g of potassium carbonate, and 5 g of dimethylsulfate was refluxed for 3 hours and drowned into 200 mL of water. The dark oil solidified overnight, and the product was collected by filtration and dried to yield 5.6 g of black solid. The weight percent assay was 83%, resulting in an assay yield of 77%. The liquid chromatograph area percentage was only 62%.

Comparative Example 1(b)

Use of Distilled 2-Hydroxy-5-Methoxybenzaldehyde

The oil from Example 1 was distilled at 10 mm through a 6-inch Vigreaux column. A light yellow fraction boiling at 124–129° C. was collected. The liquid chromatograph area percentage was 95% and the liquid chromatographic weight percentage was 90%. The overall assay yield based on the starting 4-methoxyphenol was 70%. The distilled oil was then converted to 2,5-dimethoxybenzaldehyde via the procedure in Comparative Example 1 (a). An 82% yield of light yellow crystals having a liquid chromatograph weight percent assay of 99.3% was obtained.

Example 2

Isolation of the Potassium Salt of 2-Hydroxy-5-Methoxybenzaldehyde

The black oil from Example 1 (202 g, 82% assay, 1.1 moles) was dissolved in 900 g of acetone and the solution was cooled to 0–5° C and treated dropwise with 136 g of 45% potassium hydroxide solution, holding the temperature below 5° C. The resulting slurry of bright yellow solid was stirred 30 min and filtered. The product cake was washed with 750 g of cold acetone, and dried at room temperature in a nitrogen-purged oven. A total of 210 g of bright yellow product having a weight percent assay of 91%, was obtained. The overall yield based on 4-methoxyphenol was 67%.

Example 3

Isolation of the Potassium Salt of 2-Hydroxy-5-Methoxybenzaldehyde

The above example was repeated except that 67.8 g of finely ground potassium hydroxide was used in the place of the aqueous solution. It was added at a temperature of 25–30° C. and the resulting solution was stirred for 1 hour at that temperature. The slurry was cooled to 0–5° C. and the product was isolated as in Example 2. The weight percent assay of the product was 98% and the overall yield based on the starting 4-methoxyphenol was 72%.

Example 4

Isolation of the Sodium Salt of 2-Hydroxy-5-Methoxybenzaldehyde

The black oil from Example 1 (45.9 g, 82% assay, 0.25 moles moles) was dissolved in 100 g of ethyl acetate and the solution was cooled to 0–5° C. and treated dropwise with 20 g of 50% sodium hydroxide solution, holding the temperature below 5° C. The resulting slurry of bright yellow solid was stirred 1 hour and filtered. The product cake was washed with 75 g of cold ethyl acetate, and dried at room temperature in a nitrogen-purged oven. A total of 39.1 g of bright yellow product, weight percent assay by HPLC of 72% (area % was 98.4) was obtained. The overall yield based on 4-methoxyphenol was 48%.

Example 5

Alkylation of the Potassium Salt of 2-Hydroxy-5-Methoxybenzaldehyde in Acetone

A slurry of 21.7 g of the potassium salt (90 wt % assay, 0.103 moles), 100 mL of acetone, and 15 g (0.119 moles) of dimethyl sulfate was warmed to 35–40° C. and held at that temperature for 2 hours at which point an analysis by TLC indicated that the reaction was complete. The resulting slurry was drowned into 300 mL of water and the resulting light yellow 1crystals were filtered off, washed with water, and air-dried. The weight of product was 15.1 g (88.3% yield); both the HPLC area and the HPLC weight percents were 100.

Example 6

Alkylation of the Potassium Salt of 2-Hydroxy-5-Methoxybenzaldehyde in Heptane-DMF A slurry of 21.0 g of potassium salt (90 wt % assay, 0.103 moles), 81 g of heptane, 6 g of DMF, and 18.9 g (0.15 moles)

of dimethyl sulfate was refluxed for 30 minutes at which point an analysis by TLC indicated that the reaction was complete. The resulting slurry was cooled to 50° C. and treated with 25 mL of water and 15 mL of concentrated HCl. The water phase was decanted and the product was crystallized by cooling to room temperature. After cooling to 0° C. the product was collected by filtration, washed with heptane, and dried to give 10.2 g (62% yield) of light yellow solid. Both the HPLC area and the HPLC weight percents were 100.

Example 7

Alkylation of the Potassium Salt of 2-Hydroxy-5-Methoxybenzaldehyde in Isopropyl Alcohol A slurry of 19.0 g of potassium salt (90 wt % assay, 0.09 moles), 65 g of isopropyl alcohol, 0.1 g of tetrabutylammonium bromide, and 13.9 g (0.11 moles) of dimethyl sulfate was warmed to 35–40° C. and held for 30 minute at which time an analysis by TLC indicated that the reaction was complete. The resulting slurry was treated with 65 g of water and the product slurry was cooled to 20° C. The product was collected by filtration and washed with 50% aqueous isopropyl alcohol, and dried. The product weight was 10.9 g (70% yield). Its HPLC area % assay was 99.9%; weight % was 97.5%.

Example 8

Alkylation of the Sodium Salt of 2-Hydroxy-5-Methoxybenzaldehyde in Acetone

A slurry of 7.87 g of sodium salt (73 wt % assay, 0.033 moles), 25 mL of acetone, and 5 g (0.04 moles) of dimethyl sulfate was refluxed for 3 hours at which time an analysis by TLC indicated that the reaction was complete. The resulting slurry was drowned into 200 mL of water and the resulting light yellow crystals were filtered off, washed with water, and air-dried. The weight of product was 5.1 g (88.3% yield). The HPLC weight percent was 92.5, area % was 96.

While this invention has been described in connection with preferred embodiments, it is not intended to limit the scope of the invention to the particular embodiments set forth, but on the contrary, it is intended to cover such alternatives, modifications, and equivalents as may be included within the spirit and scope of the invention as defined by the appended claims. For example, there are numerous variations and combinations of reaction conditions, e.g., component concentrations, desired solvents, solvent mixtures, temperatures, pressures and other reaction ranges and conditions that can be used to optimize the product purity and yield obtained from the described process. Also, one skilled in the art will appreciate that in practicing the process of this invention, only reasonable and routine experimentation will be required to optimize such process conditions.

What is claimed is:

1. A process for preparing 2,5-dimethoxy benzaldehyde comprising the steps of:
    (a) reacting 2-hydroxy-5-methoxy benzaldehyde with a metal hydroxide to produce a reaction mixture comprising a metal salt of 2-hydroxy-5-methoxy benzaldehyde;
    (b) separating the metal salt of 2-hydroxy-5-methoxy benzaldehyde from the reaction mixture of step (a) to obtain an at least substantially pure metal salt of 2-hydroxy-5-methoxy benzaldehyde; and
    (c) alkylating the at least substantially pure metal salt of 2-hydroxy-5-methoxy benzaldehyde from step (b) with dimethylsulfate to produce 2,5-dimethoxy benzaldehyde.

2. The process of claim 1, further comprising prior to step (a), forming 2-hydroxy-5-methoxy benzaldehyde and performing step (a) in situ with the formation of 2-hydroxy-5-methoxy benzaldehyde.

3. The process of claim 1, wherein step (b) is performed by filtering the reaction mixture of step (a).

4. The process of claim 1, wherein the metal-hydroxide is sodium hydroxide or potassium hydroxide.

5. The process of claim 1, wherein the reaction of step (a) occurs in the presence of at least one suitable first solvent.

6. The process of claim 5, wherein the at least one suitable first solvent comprises a polar organic solvent comprising an alkanol, ketone, ester of acetic acid, glycol, or ether.

7. The process of claim 5, wherein the at least one suitable first solvent comprises isopropyl alcohol, n-butanol, acetone, methyl ethyl ketone, ethyl acetate, n-propyl acetate, ethylene glycol, propylene glycol, dimethoxy ethane, dimethoxy methane, 2-methoxy ethanol or 2-hydroxy-1-methoxypropane.

8. The process of claim 5, wherein the at least one suitable first solvent comprises acetone or ethyl acetate.

9. The process of claim 1, wherein step (c) is performed in the presence of at least one suitable second solvent.

10. The process of claim 9, wherein the at least one suitable second solvent comprises an alkanol, ketone, ester of acetic acid, glycol, or ether.

11. The process of claim 9, wherein the at least one suitable second solvent comprises isopropyl alcohol, n-butanol, acetone, methyl ethyl ketone, ethyl acetate, n-propyl acetate, ethylene glycol, propylene glycol, dimethoxy ethane, dimethoxy methane, 2-methoxy ethanol or 2-hydroxy-1-methoxypropane.

12. The process of claim 9, wherein the at least one suitable second solvent comprises a mixture of heptane and dimethylformamide or a mixture of toluene and dimethylformamide.

13. The process of claim 1, wherein in step (c) the molar ratio of dimethyl sulfate to the metal salt of 2-hydroxy-5-methoxy benzaldehyde is from about 1:1 to about 2:1.

14. The process of claim 1, wherein in step (a) the molar ratio of metal hydroxide to 2-hydroxy-5-methoxy benzaldehyde is from about 0.95 to about 1.05.

15. The process of claim 1, wherein the metal hydroxide component is introduced as a concentrated solution of the metal hydroxide in water, a concentrated solution of the metal hydroxide in methanol, or a dry solid.

16. A process for preparing 2,5-dimethoxy benzaldehyde comprising the steps of:
    (a) reacting a 4-methoxy phenol, or a metal salt thereof, with formaldehyde or paraformaldehyde to form a crude reaction product comprising 2-hydroxy-5-methoxy benzaldehyde;
    (b) reacting the crude 2-hydroxy-5-methoxy benzaldehyde product from step (a) with a metal hydroxide to produce a reaction mixture comprising a metal salt of 2-hydroxy-5-methoxy benzaldehyde;
    (c) separating the metal salt of 2-hydroxy-5-methoxy benzaldehyde from the reaction mixture of step (b) to obtain an at least substantially pure metal salt of 2-hydroxy-5-methoxy benzaldehyde; and (d) alkylating the at least substantially pure metal salt of 2-hydroxy-5-methoxy benzaldehyde from step (c) with dimethylsulfate to produce 2,5-dimethoxy benzaldehyde.

17. The process according to claim 16, wherein step (b) is performed in the presence of a first solvent comprising an alkanol, ketone, ester of acetic acid, glycol, or ether, and the metal hydroxide is potassium hydroxide or sodium hydroxide; and step (d) is performed in the presence of a second solvent comprising an alkanol, ketone, ester of acetic acid, glycol, or ether.

18. The process according to claim 17 wherein the first solvent comprises acetone or ethyl acetate and the second solvent comprises a mixture of heptane and dimethylformamide or a mixture of toluene and dimethylformamide.

19. The process according to claim 16, wherein in step (b) the molar ratio of metal hydroxide to 2-hydroxy-5-methoxy benzaldehyde is from about 0.95 to about 1.05; and in step (d) the molar ratio of dimethyl sulfate to the metal salt of 2-hydroxy-5-methoxy benzaldehyde is from about 1:1 to about 2:1.

* * * * *